(12) United States Patent
Xia et al.

(10) Patent No.: US 11,826,178 B2
(45) Date of Patent: Nov. 28, 2023

(54) SYSTEMS AND METHODS FOR MOTION DETECTION

(71) Applicant: SHANGHAI UNITED IMAGING HEALTHCARE CO., LTD., Shanghai (CN)

(72) Inventors: Xinyuan Xia, Shanghai (CN); Lingzhi Hu, Houston, TX (US); Yiran Li, Houston, TX (US); Shuangyue Zhang, Shanghai (CN); Tuoyu Cao, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 32 days.

(21) Appl. No.: 17/136,081

(22) Filed: Dec. 29, 2020

(65) Prior Publication Data
US 2021/0393215 A1   Dec. 23, 2021

(30) Foreign Application Priority Data

Jun. 19, 2020 (CN) .......................... 202010566383.4
Jun. 19, 2020 (CN) .......................... 202021158154.0

(51) Int. Cl.
*A61B 5/00* (2006.01)
*A61B 5/11* (2006.01)
*A61B 5/113* (2006.01)
*G01S 13/50* (2006.01)
*A61B 5/055* (2006.01)

(52) U.S. Cl.
CPC ............ *A61B 5/7292* (2013.01); *A61B 5/055* (2013.01); *A61B 5/1102* (2013.01); *A61B 5/113* (2013.01); *A61B 5/1116* (2013.01); *A61B 5/1126* (2013.01); *G01S 13/50* (2013.01)

(58) Field of Classification Search
None
See application file for complete search history.

(56) References Cited

U.S. PATENT DOCUMENTS

2016/0135694 A1\*  5/2016  van Dorp ............. A61B 5/7278
                                                                    600/430
2021/0298643 A1\*  9/2021  Baker .................. A61B 5/0004

FOREIGN PATENT DOCUMENTS

EP            3550327 A1 \* 10/2019  ........... A61N 5/1049

OTHER PUBLICATIONS

Hilger et al., "ultraMEDIS—Ultra-Wideband Sensing in Medicine," (Mar. 2013), Ultra-Wideband Radio Technologies for Communications, Localization and Sensor Applications, ISBN: 979-953-307-275-2. (Year: 2013).\*

\* cited by examiner

*Primary Examiner* — Joel Lamprecht
*Assistant Examiner* — Ashish S Jasani
(74) *Attorney, Agent, or Firm* — METIS IP LLC

(57) ABSTRACT

The present disclosure is related to systems and methods for motion detection. The method includes obtaining, via at least one detection device, detection data of a subject located in a field of view (FOV) of a medical device. The method also includes determining motion data of the subject based on the detection data.

18 Claims, 11 Drawing Sheets

SYSTEMS AND METHODS FOR MOTION DETECTION

CROSS-REFERENCE TO RELATED APPLICATIONS

This application claims priority of Chinese Patent Application No. 202010566383.4, filed on Jun. 19, 2020, Chinese Patent Application No. 202021158154.0, filed on Jun. 19, 2020, and the contents of each of which are hereby incorporated by reference.

TECHNICAL FIELD

This disclosure generally relates to systems and methods for medical imaging, and more particularly, relates to systems and methods for motion detection in medical imaging.

BACKGROUND

Medical systems, such as CT scanners, MRI scanners, PET scanners, are widely used for creating images of interior of a patient's body for, e.g., medical diagnosis and/or treatment purposes. A motion (e.g., a posture motion, a physiological motion) of the subject during a scan may affect imaging quality by causing, for example, motion artifacts in a resulting image, which in turn may hinder an accurate detection, localization, and/or quantification of possible lesions (e.g., a tumor). Therefore, it is desirable to provide effective systems or methods for motion detection in the medical imaging.

SUMMARY

According to an aspect of the present disclosure, a method for motion detection may be implemented on a computing device having at least one processor and at least one storage device. The method may include obtaining, via at least one detection device, detection data of a subject located in a field of view (FOV) of a medical device. The method may include determining motion data of the subject based on the detection data.

In some embodiments, the motion data may include posture data of the subject and physiological motion data of the subject.

In some embodiments, the method may include extracting the posture data of the subject from the detection data. The method may include extracting the physiological motion data of the subject from the detection data.

In some embodiments, the method may include determining contour data of the subject based on the detection data. The method may include determining the posture data based on the contour data.

In some embodiments, the method may include extracting the cardiac motion data from the detection data. The method may include extracting the respiratory motion data from the detection data.

In some embodiments, the method may include generating, based on the motion data, a control signal for controlling the medical device to scan the subject.

In some embodiments, the control signal may involve a gating technique.

In some embodiments, the method may include causing the medical device to perform, according to the control signal, a scan on the subject. The method may include generating an image of the subject based on the scan. The method may include performing an artifact correction on the image of the subject based on the motion data.

In some embodiments, the method may include determining a region of interest (ROI) of the subject. The method may include extracting, from the detection data of the subject, a detection data sub-set of the ROI of the subject. The method may include determining the motion data of the subject based on the detection data sub-set of the ROI of the subject.

In some embodiments, the at least one detection device may include a plurality of detection devices. The method may include obtaining a detection data sub-set from each of the plurality of detection devices. The detection data sub-set may be acquired by monitoring, via the each detection device, at least part of the subject in an FOV of the each detection device. The method may include obtaining the detection data of the subject by merging, based on the FOV of the each detection device, the detection data sub-sets of the plurality of detection devices.

In some embodiments, the at least one detection device may include a frequency modulated continuous wave (FMCW) radar.

In some embodiments, an emission frequency of the FMCW radar may be greater than 60 GHz.

In some embodiments, the medical device may be a magnetic resonance imaging (MRI) device.

In some embodiments, the at least one detection device may be mounted on a radiofrequency (RF) coil of the MRI device.

According to another aspect of the present disclosure, a system for motion detection may include at least one storage device storing a set of instructions, and at least one processor in communication with the at least one storage device. When executing the stored set of instructions, the at least one processor may cause the system to perform a method. The method may include obtaining, via at least one detection device, detection data of a subject located in a field of view (FOV) of a medical device. The method may include determining motion data of the subject based on the detection data.

According to still another aspect of the present disclosure, a non-transitory computer readable medium may include at least one set of instructions. When executed by at least one processor of a computing device, the at least one set of instructions may cause the at least one processor to effectuate a method. The method may include obtaining, via at least one detection device, detection data of a subject located in a field of view (FOV) of a medical device. The method may include determining motion data of the subject based on the detection data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
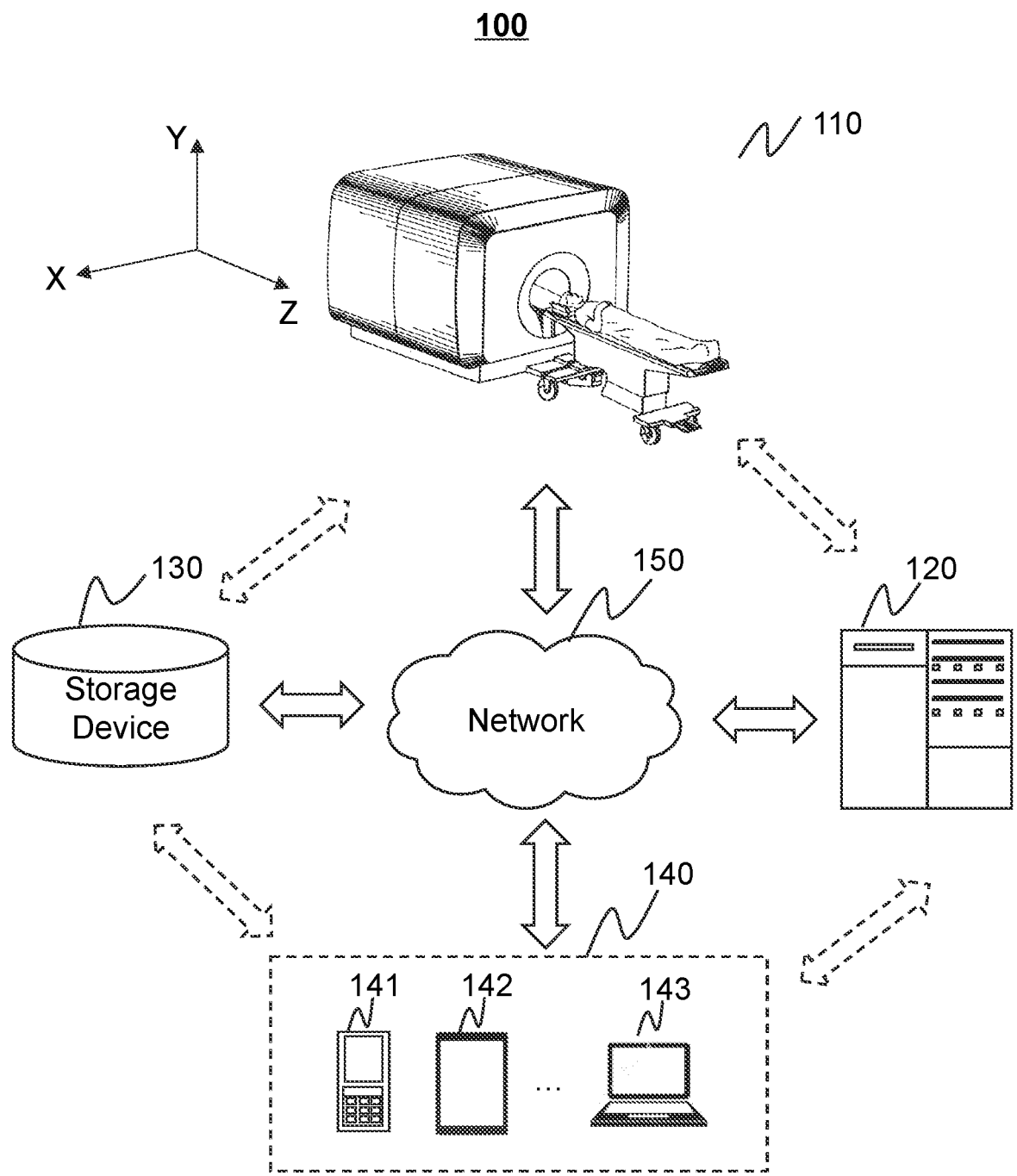
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "anatomical structure" in the present disclosure may refer to gas (e.g., air), liquid (e.g., water), solid (e.g., stone), cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body. The term "an image of a subject" may be referred to as the subject for brevity.

An aspect of the present disclosure relates to a system and method for motion detection in a medical procedure. According to some embodiments of the present disclosure, a processing device may obtain, via at least one detection device (e.g., a frequency modulated continuous wave (FMCW) radar), detection data of a subject located in a field of view (FOV) of a medical device. As used herein, an FOV of a medical device refers to an area or region scanned by the medical device during a scan of a subject. The medical device may include an imaging device, a treatment device, or a combination thereof. A scan of a subject by a medical device may include an imaging scan or a treatment of the subject using the medical device. The processing device may determine motion data (e.g., posture data, physiological motion data) of the subject based on the detection data.

In some embodiments, the at least one detection device may be a non-contact detection device mounted outside of the FOV of the medical device. As used herein, a non-contact detection device indicates that the detection device does not need to be in contact with a subject when detecting data relating to a motion of the subject (or referred to as motion data) or that the detection of motion data of the subject by the detection device does not depend on the detection device being in contact with the subject. For example, the medical device may be a magnetic resonance imaging (MRI) device, and the at least one detection device may be mounted on a radio frequency (RF) coil of the MRI device. In some embodiments, the processing device 120 may generate, based on the motion data, a control signal for controlling the medical device to scan the subject. The processing device may generate an image of the subject by causing the medical device to perform, according to the control signal, a scan on the subject. The processing device may perform an artifact correction on the image of the subject based on the motion data.

Accordingly, the posture data and the physiological motion data of the subject may be detected by the at least one detection device simultaneously. The medical device may be controlled based on the posture data and/or the physiological motion data. In addition, the signal interference between the at least one detection device and the medical device may be reduced or eliminated by mounting the at least one detection device outside of the FOV of the medical device. Furthermore, in a conventional way, during a scan of a subject, one or more electrodes and/or respiratory zones may be attached to the body of the subject in order to detect the physiological motion of the subject, which may cause discomfort to the subject. Compared to a contact detection device (in which the detection device needs to be in contact with a subject for detecting motion data of the subject), the non-contact detection device disclosed herein may reduce the discomfort of the subject, and/or avoiding the procedure and time needed for setting up such a contact detection device on the subject, which may reduce the setup time of the medical device.

FIG. 1 is a schematic diagram illustrating an exemplary medical system according to some embodiments of the present disclosure. As illustrated, a medical system 100 may include a medical device 110, a processing device 120, a storage device 130, a terminal 140, and a network 150. The components of the medical system 100 may be connected in one or more of various ways. Merely by way of example, as illustrated in FIG. 1, the medical device 110 may be connected to the processing device 120 directly as indicated by the bi-directional arrow in dotted lines linking the medical device 110 and the processing device 120, or through the network 150. As another example, the storage device 130 may be connected to the medical device 110 directly as indicated by the bi-directional arrow in dotted lines linking the medical device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The medical device 110 may be configured to acquire imaging data relating to a subject. The imaging data relating to a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made object, etc. As another example, the subject may include a specific portion, an organ, and/or tissue of the patient. Specifically, the subject may include the head, the neck, the thorax, the heart, the stomach, a blood vessel, soft tissue, a tumor, or the like, or any combination thereof. In the present disclosure, "object" and "subject" are used interchangeably.

In some embodiments, the medical device 110 may include a single modality imaging device. For example, the medical device 110 may include a positron emission tomography (PET) device, a single-photon emission computed tomography (SPECT) device, a magnetic resonance imaging (MRI) device (also referred to as an MR device, an MR scanner), a computed tomography (CT) device, an ultrasound (US) device, an X-ray imaging device, or the like, or any combination thereof. In some embodiments, the medical device 110 may include a multi-modality imaging device.

Exemplary multi-modality imaging devices may include a PET-CT device, a PET-MRI device, a SPET-CT device, or the like, or any combination thereof. The multi-modality imaging device may perform multi-modality imaging simultaneously. For example, the PET-CT device may generate structural X-ray CT data and functional PET data simultaneously in a single scan. The PET-MRI device may generate MRI data and PET data simultaneously in a single scan.

In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the medical device 110 seen from the direction facing the front of the medical device 110; the positive Y direction along the Y axis shown in FIG. 1 may be from the lower part to the upper part of the medical device 110; the positive Z direction along the Z axis shown in FIG. 1 may refer to a direction in which the object is moved out of a scanning channel (or referred to as a bore) of the medical device 110.

Merely by way of example, the medical device may be an MRI device. The MRI device may scan a subject located within its FOV and generate MR image data relating to the subject. The MR image data may include k-space data, MR signals, an MR image, etc. The MR image data may be acquired by the MRI device via scanning the subject using a pulse sequence. Exemplary pulse sequences may include a spin-echo sequence, a gradient echo sequence, a diffusion sequence, an inversion recovery sequence, or the like, or any combination thereof. For example, the spin-echo sequence may include a fast spin-echo (FSE), a turbo spin-echo (TSE), a rapid acquisition with relaxation enhancement (RARE), a half-Fourier acquisition single-shot turbo spin-echo (HASTE), a turbo gradient spin echo (TGSE), or the like, or a combination thereof. More descriptions of the MRI device may be found elsewhere in the present disclosure (e.g., FIG. 2, and the descriptions thereof).

The processing device 120 may process data and/or information obtained from the medical device 110, the storage device 130, and/or the terminal(s) 140. For example, the processing device 120 may obtain, via at least one detection device, detection data of a subject located in an FOV of a medical device (e.g., the medical device 110). As another example, the processing device 120 may determine motion data of a subject based on detection data. In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical device 110.

The storage device 130 may store data, instructions, and/or any other information. In some embodiments, the storage device 130 may store data obtained from the medical device 110, the processing device 120, and/or the terminal(s) 140. The data may include image data acquired by the processing device 120, algorithms and/or models for processing the image data, etc. For example, the storage device 130 may store detection data of a subject obtained from one or more detection devices. As another example, the storage device 130 may store motion data of a subject determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), a high-speed RAM, etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140). One or more components in the medical system 100 may access the data or instructions stored in the storage device 130 via the network 150. In some embodiments, the storage device 130 may be integrated into the medical device 110.

The terminal(s) 140 may be connected to and/or communicate with the medical device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 and/or the terminal 140 may obtain an image from the medical device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the medical system 100 may further include a transmission device configured to receive or transmit data via a network (e.g., the network 150). For example, the transmission device may include a network adapter (e.g., a network interface controller), which may be connected to other devices via a base station to communicate with the Internet. As another example, the transmission device may include an RF module, which may communicate with the Internet in a wireless manner. In some embodiments, the medical system 100 may further include one or more detection devices (e.g., a detection device 30 illustrated in FIGS. 2, 4-7) configured to monitor a motion of a subject before and/or during a scan of the subject, and generate detection data of the subject. More descriptions of the detection device may be found elsewhere in the present disclosure (e.g., FIGS. 2-7, and the descriptions thereof).

Figure 2:
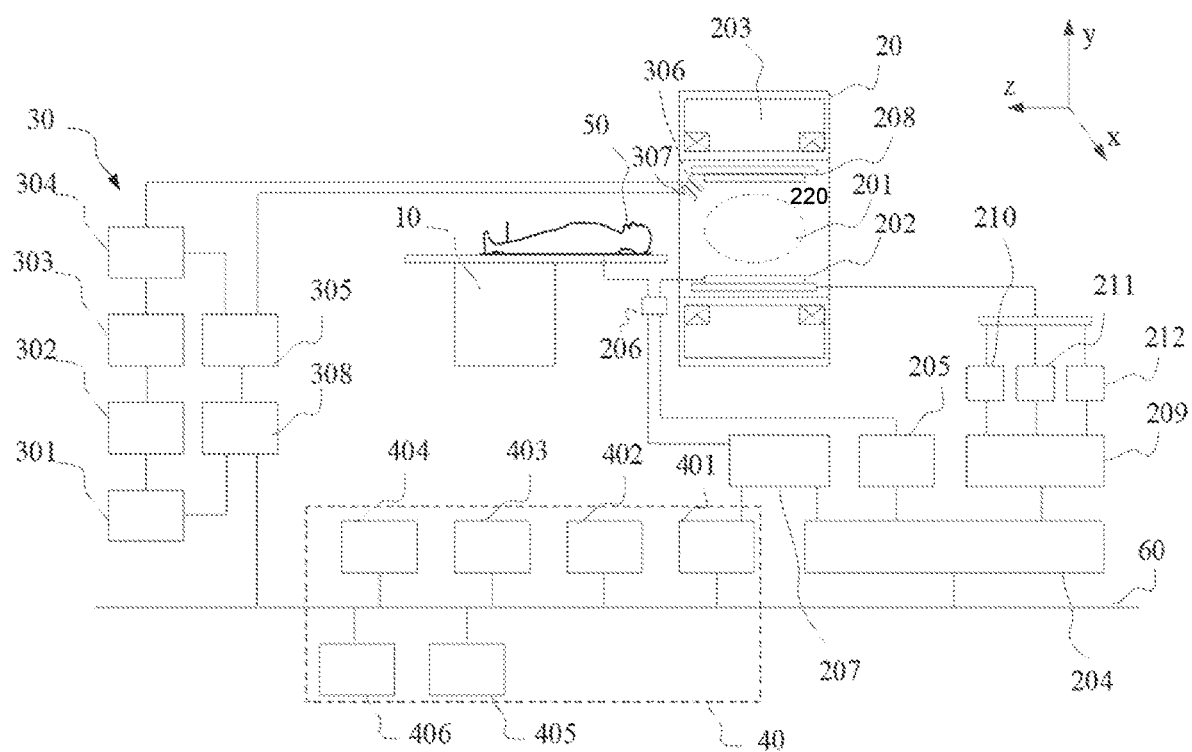
FIG. 2 is a schematic diagram illustrating an exemplary medical system according to some embodiments of the present disclosure.

FIG. 2 is a schematic diagram illustrating an exemplary medical system according to some embodiments of the present disclosure. As illustrated, a medical system 200 may include a scanning table 10, an MRI device 20, at least one detection device 30, and a computing device 40.

The MRI device 20 may be configured to scan a subject 50 located in its FOV 201 and generate MR image data relating to the subject 50. For example, the subject 50 may be placed on the scanning table 10 and be moved within the FOV 201 of the MRI device 20. In some embodiments, the MRI device 20 may form a scanning cavity 220 that the subject 50 is placed within. In some embodiments, the MRI device 20 may include an RF coil assembly 202, a main magnet assembly 203, a pulse control unit 204, an RF pulse generator 205, a switch control unit 206, an RF receiving unit 207, a gradient coil assembly 208, and a gradient signal generation unit 209.

The main magnet assembly 203 may generate a first magnetic field (or referred to as a main magnetic field) that may be applied to a subject (e.g., the subject 50) exposed inside the field. The main magnet assembly 203 may include a resistive magnet or a superconductive magnet that both need a power supply (not shown) for operation. Alternatively, the main magnet assembly 203 may include a permanent magnet. The main magnet assembly 203 may have any magnetic field intensity, for example, 0.2 Tesla, 0.5 Tesla, 1.0 Tesla, 1.5 Tesla, and 3.0 Tesla. The main magnet assembly 203 may include a bore that the subject is placed within. The main magnet assembly 203 may also control the homogeneity of the generated main magnetic field. Some shim coils may be in the main magnet assembly 203. The shim coils placed in the gap of the main magnet assembly 203 may compensate for the inhomogeneity of the magnetic field of the main magnet assembly 203. The shim coils may be energized by a shim power supply.

The gradient coil assembly 208 may be located inside the main magnet assembly 203. The gradient coil assembly 208 may generate a second magnetic field (or referred to as a gradient field, including gradient fields Gx, Gy, and Gz). The second magnetic field may be superimposed on the main field generated by the main magnet assembly 203 and distort the main field so that the magnetic orientations of the protons of a subject (e.g., the subject 50) may vary as a function of their positions inside the gradient field, thereby encoding spatial information into MR signals generated by the region of the subject being imaged. The gradient coil assembly 208 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coil assembly 208 may allow spatial encoding of MR signals for image construction. The gradient coil assembly 208 may be connected with one or more of an X gradient amplifier 210, a Y gradient amplifier 211, or a Z gradient amplifier 212. One or more of the three amplifiers may be connected to the gradient signal generation unit 209. The pulse control unit 204 may control the gradient signal generation unit 209 to generate gradient signals that are applied to the X gradient amplifier 210, the Y gradient amplifier 211, and/or the Z gradient amplifier 212. An amplifier may amplify a gradient signal. An amplified gradient signal may be applied to one of the coils in the gradient coil assembly 208 to generate a magnetic field in the X-axis, the Y-axis, or the Z-axis, respectively. The gradient coil assembly 208 may be designed for either a close-bore MRI scanner or an open-bore MRI scanner. In some instances, all three sets of coils of the gradient coil assembly 208 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, the RF coil assembly 202 may be located inside the main magnet assembly 203 and serve as transmitters, receivers, or both. In some embodiments, the RF coil assembly 202 may include a plurality of RF coils. The RF coils may include one or more RF transmit coils and/or one or more RF receiver coils. The RF transmit coil(s) may transmit RF pulses to the subject. Under the coordinated action of the main magnetic field, the gradient magnetic field, and the RF pulses, MR signals relating to the subject (e.g., the subject 50) may be generated. The RF receiver coils may receive MR signals from the subject. In some embodiments, one or more RF coils may both transmit RF pulses and receive MR signals at different times. In some embodiments, the function, size, type, geometry, position, amount, and/or magnitude of the RF coil(s) may be determined or changed according to one or more specific conditions. For example, according to the difference in function and size, the RF coil(s) may be classified as volume coils and local coils. The term "volume coil" as used herein generally refers to coils that are used to provide a homogenous RF excitation field across a relatively large volume, such as to cover the entire target body. For example, many commercially available MRI scanners include a volume coil that is big enough for whole body imaging of a human subject, thus sometimes is referred to as the "body coil". The term "local coil" as used herein generally refers to coils that are to be placed in close proximity to the region of interest during MR imaging. The local coils may be designed to achieve improved RF detection sensitivity over a small region of interest. In some embodiments, an RF receiver coil may correspond to a channel. The RF receiver coil(s) may receive a plurality of channels of MR signals from the subject. The received MR signal(s) may be sent to the computing device 40 for image reconstruction and/or image processing.

In some embodiments, during the MR imaging of the subject, a strong uniform main magnetic field provided by the main magnet assembly 203 may align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., RF signals generated by the RF coil assembly 202). For example, the pulse control unit 204 may control the RF pulse generator 205 to generate an RF pulse. The RF pulse may be amplified by an amplifier, and an amplified RF pulse may be applied to the RF coil assembly 202 via switch control unit 206 to generate the RF signals. When the additional magnetic field is removed, the magnetic moments of the H atoms rotate back into alignment with the main magnetic field thereby emitting an MR signal. The MR signal generated by the subject may be sensed by the RF coil assembly 202 or the RF receiving unit 207. The MR signals may be digitized, processed, and sent to the computing device 40 to reconstruct an image.

In some embodiments, the gradient coil assembly 208 and the RF coil assembly 202 may be circumferentially positioned with respect to the subject 50. It is understood by those skilled in the art that the main magnet assembly 203, the gradient coil assembly 208 and the RF coil assembly 202 may be situated in a variety of configurations around the subject 50.

The detection device 30 may be configured to obtain detection data relating to a motion (e.g., a posture motion, a physiological motion) of the subject 50 before and/or during a scan (e.g., an MR scan) of the subject 50. In some embodiments, the detection device 30 may be a non-contact detection device. For example, the detection device 30 may include a radar. In some embodiments, an emission frequency of the radar may be greater than 60 GHz. A high frequency range (e.g., 60 GHz-80 GHz) of the radar may be used to detect a body surface movement (e.g., a skin movement) of the subject 50. The radar may emit a reference signal (e.g., an RF sweep signal) to an FOV of the radar, and the reference signal may be reflected by the subject 50 located in the FOV of the radar. The radar may receive at least a portion of the reflected reference signal (e.g., an RF echo signal) from the subject 50. In some embodiments, the reference signal may be a continuous wave signal with a time-varying frequency. For example, the frequency of the reference signal may have a linear change or a stepping change over time.

The detection data may include the reference signal, the received reflected reference signal, image data (e.g., point-cloud data) generated based on the reference signal and the received reflected reference signal, or the like, or any combination thereof. Information (e.g., a frequency difference, a phase difference) relating to the reflected reference signal and the reference signal may reflect feature information of the subject 50 (e.g., a range of the subject 50, a distance between the subject 50 and the radar) and a motion of the subject 50 (e.g., a moving velocity, a moving direction, a displacement of the subject 50 from a reference position), and be used to determine motion data of the subject 50. More descriptions of the determination of the motion data may be found elsewhere in the present disclosure (e.g., FIG. 11 and descriptions thereof).

For example, the detection device 30 may include a microwave radar device, a millimeter-wave radar device, a centimeter-wave radar device, or the like. As another example, the detection device 30 may include a modulated continuous wave radar (e.g., a frequency modulated continuous wave (FMCW) radar), an unmodulated continuous-wave radar, or the like. As used herein, an FMCW radar refers to a type of radar which radiates continuous transmission power, and can change its operating frequency during the measurement; that is, the transmission signal is modulated in frequency (or in phase). Merely by way of example, the FMCW radar may include one or more transmitting antennas and one or more receiving antennas. The one or more transmitting antennas may emit a plurality of RF sweep signals with linearly varying frequencies. At least a portion of the plurality of RF sweep signals may be reflected by the surface of the subject 50, and a plurality of RF echo signals may be generated. The one or more receiving antennas may receive the plurality of RF echo signals.

In some embodiments, as illustrated in FIG. 2, the detection device 30 (e.g., an FMCW radar) may include a clock generator 301, a digitally controlled oscillator 302, a signal processing unit 303, a coupler 304, a mixer 305, a transmitting antenna 306, a receiving antenna 307, and a digital signal processor 308. The clock generator 301 operably connected to the digitally controlled oscillator 302, may be configured to generate a reference clock signal. The digital controlled oscillator 302 operably connected to the signal processing unit 303 and the digital signal processor 308, respectively, may be configured to generate a digital frequency sweep signal with a preset frequency bandwidth based on the reference clock signal and one or more waveform parameters output by the digital signal processor 308. The signal processing unit 303 operably connected to the transmitting antenna 306 and the mixer 305 via the coupler 304, respectively, may be configured to convert the digital frequency sweep signal into an analog sweep signal, and modulate the analog sweep signal to an RF to obtain an RF sweep signal. The transmitting antenna 306 may be configured to emit the RF sweep signal to the FOV 201. The receiving antenna 307 operably connected to the mixer 305 may be configured to receive an RF echo signal reflected from the surface of the subject 50. The digital signal processor 308 operably connected to the mixer 305 and the digitally controlled oscillator 302, respectively, may be configured to determine motion data of the subject 50 based on the RF sweep signal and the RF echo signal.

In some embodiments, the detection device 30 may include an analog device and/or a digital chip. For example, the detection device 30 may include a housing and a circuit board. The circuit board may be accommodated in the housing, and one or more FMCW radars may be operably connected to the circuit board. Accordingly, the detection device 30 may be integrated into a relatively independent module to facilitate multi-module expansion and installation. In some embodiments, the detection device 30 may be realized by a digital circuit. For example, the detection device 30 may be integrated into a digital chip, and one or more transmitting antennas and one or more receiving antennas may be peripheral components of the digital chip. Accordingly, the detection device 30 may be integrated and digitized, and the volume of the detection device 30 may further be reduced.

In some embodiments, the detection device 30 may be mounted at one or more of various suitable locations for monitoring the motion of the subject 50. In some embodiments, the mounting location of the detection device 30 may be determined based on an FOV of the detection device 30, feature information (e.g., a location, a length, a width, a height) of the scanning table 10, and/or an FOV of the MRI device 20. For example, the detection device 30 may be mounted at a specific location such that the FOV of the detection device 30 can cover the entire range of the scanning table 10. As another example, the detection device 30 may be mounted at a specific location such that the FOV of the detection device 30 can cover at least part of the FOV of the MRI device 20.

Figure 4:
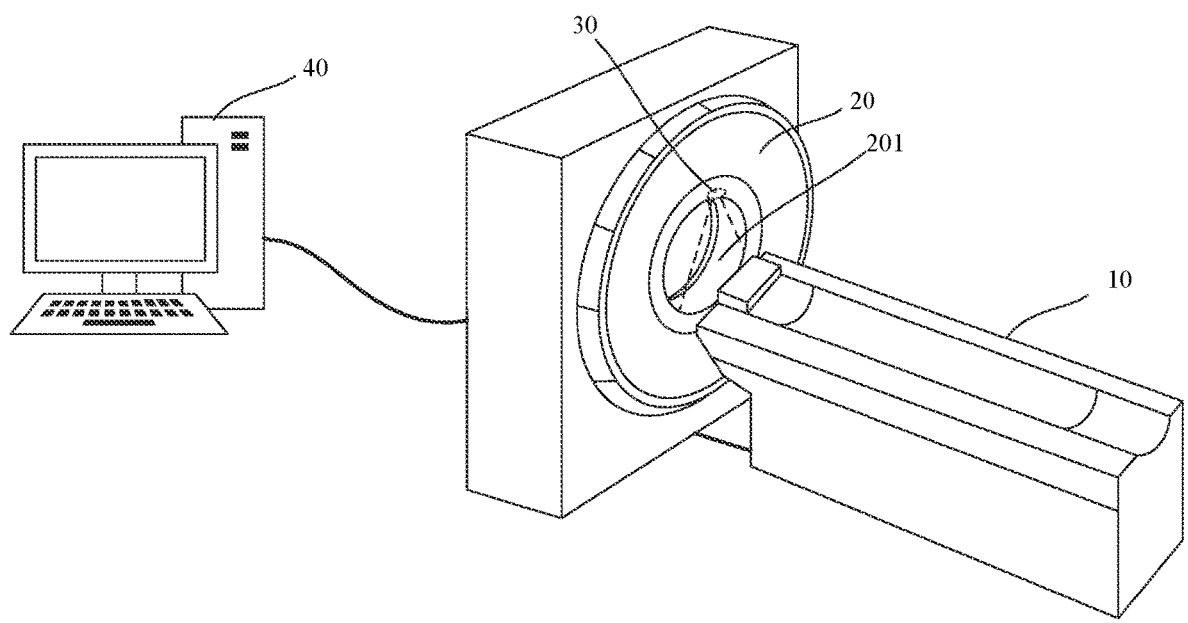
FIG. 4 is a schematic diagram illustrating an exemplary medical system according to some embodiments of the present disclosure.
Figure 5:
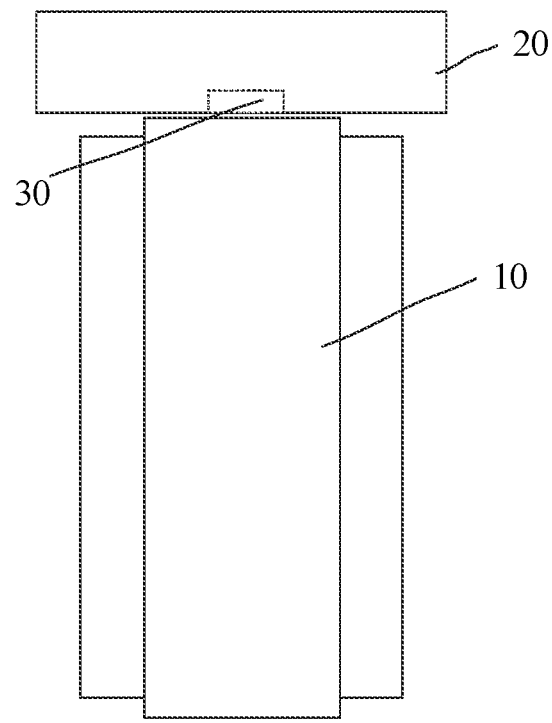
FIG. 5 is a schematic diagram illustrating a top view of an exemplary medical system according to some embodiments of the present disclosure.
Figure 6:
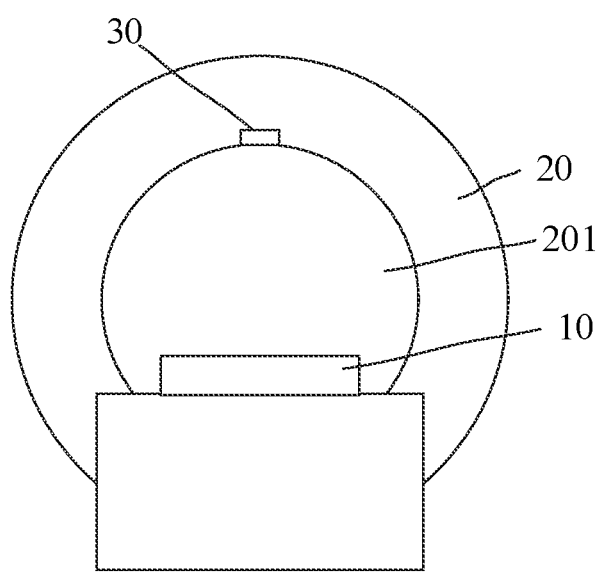
FIG. 6 is a schematic diagram illustrating an exemplary medical system according to some embodiments of the present disclosure.

In some embodiments, the detection device 30 may be integrated into or mounted on the MRI device 20. In some embodiments, the detection device 30 may be mounted outside the FOV 201 of the MRI device 20 (e.g., on the RF coil assembly 202, on the main magnet assembly 203), in order to reduce or eliminate the signal interference between the detection device 30 and the MRI device 20. For example, the detection device 30 may be mounted on an upper portion of the scanning cavity 220 (e.g., a position of the scanning cavity 220 directly above the scanning table 10) of the MRI device 20 to monitor the subject 50 on the scanning table 10, as illustrated in FIGS. 4-6. As another example, the detection device 30 may be mounted on a side portion of the scanning cavity 220 of the MRI device 20 to monitor the subject 50 on the scanning table 10. As still another example, a plurality of detection devices 30 may be mounted on different portions of the scanning cavity 220 (e.g., different positions of the scanning cavity 220 above the scanning table 10) to monitor the subject 50 from different directions. A number (or count) of the detection devices 30 may be determined based on an FOV of the detection device 30, an FOV of the MRI device 20, a mounting location of the detection device 30, and/or an installation space of the detection device 30 in the scanning cavity 220 of the MRI device 20. In some embodiments, each of the plurality of detection devices 30 may be mounted at a specific location such that a total FOV of the plurality of detection devices 30 can cover the FOV of the MRI device 20. Merely by way of example, the plurality of detection devices 30 may be mounted on different positions of the scanning cavity 220 above the scanning table 10, and distributed on both sides of an axial direction (e.g., the Z-axis direction) of the MRI device 20, so as to make a full use of the installation space of the scanning cavity 220, and ensure that the total FOV of the plurality of detection devices 30 can cover the FOV of the MRI device 20.

Figure 7:
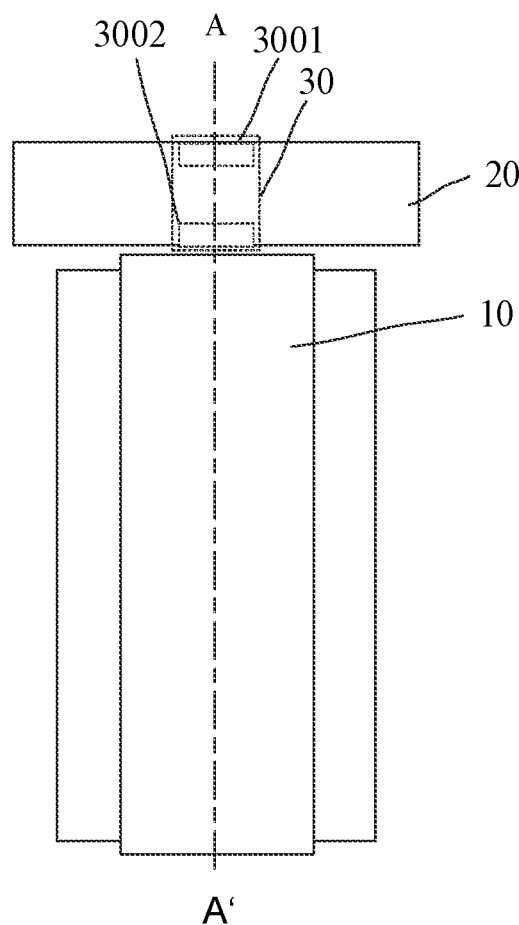
FIG. 7 is a schematic diagram illustrating a top view of an exemplary medical system according to some embodiments of the present disclosure.

For illustration purposes, as illustrated in FIG. 7, a first detection device 3001 and a second detection device 3002 may be mounted on an upper portion of the scanning cavity 220 of the MRI device 20 to monitor the front surface of the subject 50 on the scanning table 10. The first detection device 3001 and the second detection device 3002 may be mounted along an axial direction (e.g., a A-A' direction illustrated in FIG. 7) of the MRI device 20. At least part of the first detection device 3001 (and/or the second detection device 3002) may be integrated into the MRI device 20. In some embodiments, a first FOV of the first detection device 3001 and a second FOV of the second detection device 3002 may not overlap, partially overlap, or completely overlap. In some embodiments, the FOV of the MRI device 20 may be covered by RF sweep signals emitted by the first detection device 3001 and RF sweep signals emitted by the second detection device 3002. The RF sweep signals emitted by the first detection device 3001 and the RF sweep signals emitted by the second detection device 3002 at the same time do not interfere with each other.

The computing device 40 may include an image reconstruction unit 401, a processor 402, a display unit 403, an input/output (I/O) device 404, a storage 405, and a communication port 406. In some embodiments, the pulse control unit 204, the image reconstruction unit 401, the processor 402, the display unit 403, the I/O device 404, the storage 405, and the communication port 406 may transmit data and/or information via a communication bus 60 to realize the control of an MR imaging process.

The image reconstruction unit 401 may be configured to reconstruct an image based on data obtained from the MRI device 20 and/or the at least one detection device 30. For example, the image reconstruction unit 401 may generate an MRI image of the subject 50 based on MRI data and motion data of the subject 50. The processor 402 may process data and/or information obtained from the MRI device 20 and/or the at least one detection device 30. For example, the processor 402 may determine motion data of the subject 50 based on the detection data obtained from the at least one detection device 30 (e.g., the digital signal processor 308). As another example, the processor 402 may generate, based on the motion data, a control signal for controlling the MRI device 20 to scan the subject 50. The processor 402 may be similar to the processing device 120 described in connection with FIG. 1, the descriptions of which are not repeated here.

The display unit 403 may be configured to display data and/or information obtained from the MRI device 20 and/or the at least one detection device 30. For example, the display unit 403 may display an MRI image of the subject 50. As another example, the display unit 403 may display motion data of the subject 50. The display unit 403 may be similar to the display 920 described in connection with FIG. 9, the descriptions of which are not repeated here.

The I/O device 404 may input and/or output signals, data, information, etc. In some embodiments, the I/O device 404 may enable a user interaction with the processor 402. In some embodiments, the I/O device 404 may include an input device and an output device. The I/O device 404 may be similar to the I/O device 830 described in connection with FIG. 8, or the I/O 950 described in connection with FIG. 9, the descriptions of which are not repeated here.

The storage 405 may store data/information obtained from the MRI device 20 and/or the at least one detection device 30. The storage 405 may be similar to the storage device 130 described in connection with FIG. 1, the descriptions of which are not repeated here.

The communication port 406 may be connected to a network to facilitate data communications. The communication port 406 may establish connections between the processor 402 and the image reconstruction unit 401, the display unit 403, the I/O device 404, the storage 405, the MRI device 20, and/or the at least one detection device 30. The communication port 406 may be similar to the communication port 840 described in connection with FIG. 8, the descriptions of which are not repeated here.

The communication bus 60 may include hardware, software, or a combination thereof. The communication bus 60 may connect the components of the medical system 200 to each other. The communication bus 60 may include a data bus, an address bus, a control bus, an expansion bus, a local bus, or the like, or any combination thereof.

It should be noted that the above description of the medical system is merely provided for the purposes of illustration, and not intended to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the RF sweep signal may be generated by other sweep signal generation techniques. For example, a direct digital frequency synthesis technique may be used to generate a digital frequency sweep signal, and the signal processing unit 303 may convert the digital frequency sweep signal into an analog sweep signal, and modulate the analog sweep signal to the RF to obtain an RF sweep signal.

Figure 3:
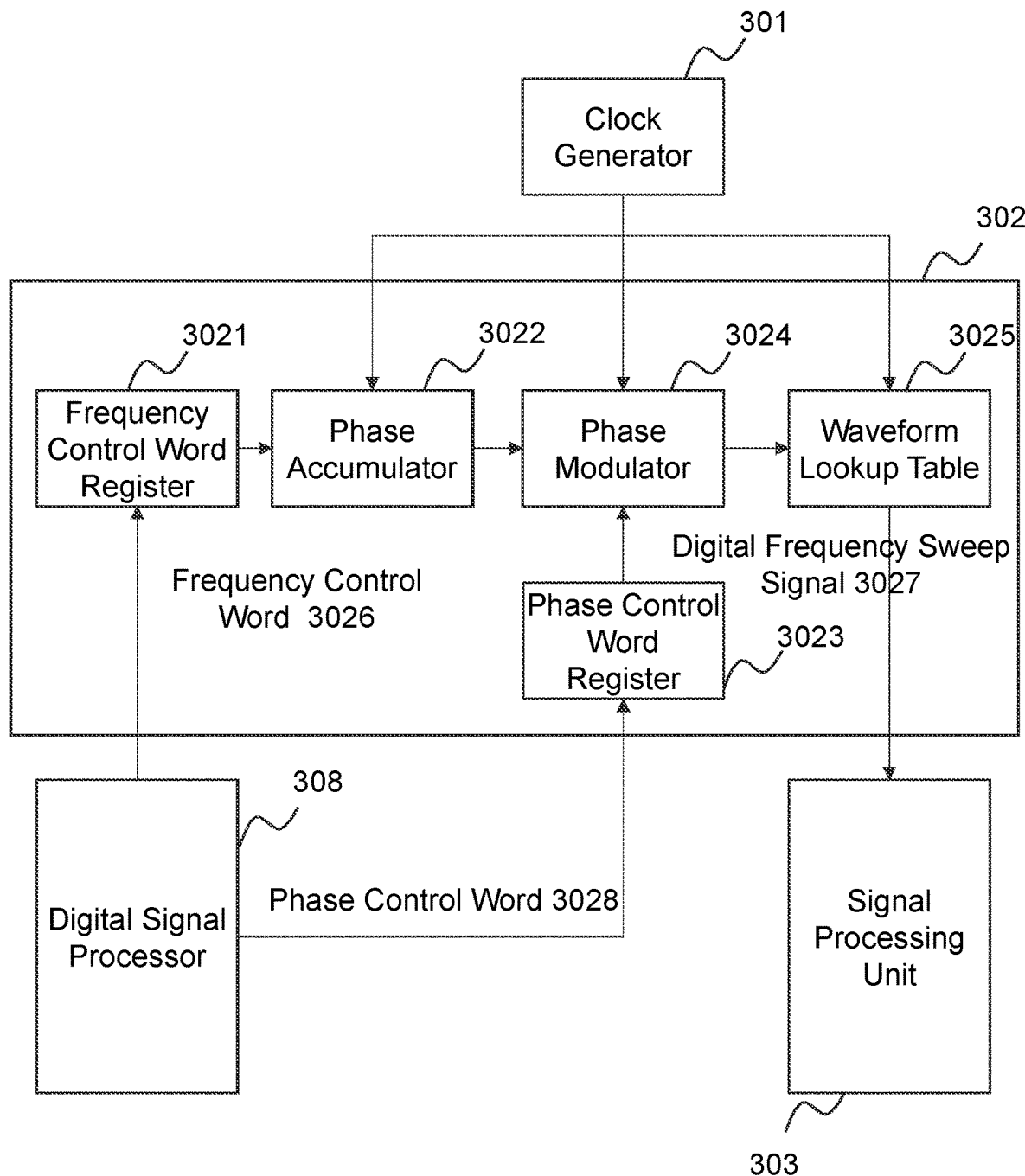
FIG. 3 is a schematic diagram illustrating an exemplary digitally controlled oscillator according to some embodiments of the present disclosure.

FIG. 3 is a schematic diagram illustrating an exemplary digitally controlled oscillator according to some embodiments of the present disclosure.

As shown in FIG. 3, the digitally controlled oscillator 302 may include a frequency control word register 3021, a phase accumulator 3022, a phase control word register 3023, a phase modulator 3024, and a waveform look-up table 3025. The frequency control word register 3021, the phase accumulator 3022, the phase modulator 3024, and the waveform look-up table 3025 may be connected in sequence. The phase control word register 3023 may be connected to the phase modulator 3024. The clock generator 301 may be connected to the phase accumulator 3022, the phase modulator 3024 and the waveform look-up table 3025, respectively. The digital signal processor 308 may be connected to the frequency control word register 3021 and the phase control word register 3023 respectively. The waveform look-up table 3025 may be connected to the signal processing unit 303.

A phase accumulation increment may correspond to a frequency control word 3026 stored in the frequency control word register 3021. The phase accumulation increment may be used to control a sweep rate of a digital frequency sweep signal 3027. A phase offset may correspond to a phase control word 3028 stored in the phase control word register 3023. The phase offset may change within a preset phase offset range. The phase offset may control the working frequency point of a digital signal to change in a corresponding frequency bandwidth. The digital signal may be generated by the phase modulator 3024. The frequency control word 3026 and the phase control word 3028 may be determined based on one or more waveform parameters output by the digital signal processor 308.

According to some embodiments of the present disclosure, a phase offset of a reference clock signal generated by the clock generator 301 may be continuously changed by adjusting the phase control word 3028 stored in the phase control word register 3023. The sweep rate of the digital frequency sweep signal 3027 may be controlled by adjusting the frequency control word 3026 stored in the frequency control word register 3021. The frequency control word 3026 may be adjusted using the digitally controlled oscillator 302 according to a direct digital frequency synthesis technique. The digital frequency sweep signal 3027 with the preset frequency bandwidth may be obtained. In some embodiments, the frequency bandwidth may be in the range from 100 MHz to 150 MHz. The digital frequency sweep signal 3027 may have a rising portion whose frequency rises linearly and gradually, and a falling portion whose frequency falls linearly and gradually.

In some embodiments, the signal processing unit 303 may further convert the digital frequency sweep signal into an analog sweep signal, and modulate the analog sweep signal to an RF to obtain an RF sweep signal. In some embodiments, the frequency of the RF sweep signal may be greater than 60 GHz.

Figure 8:
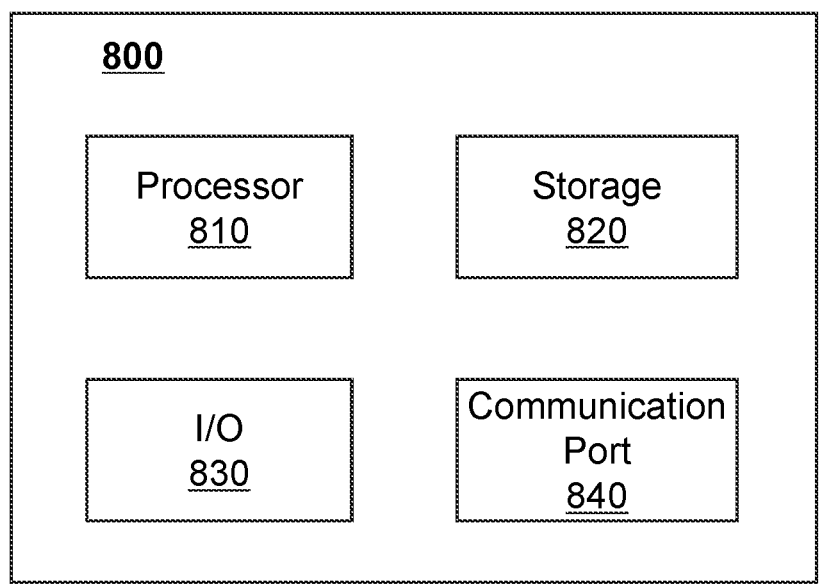
FIG. 8 is a schematic diagram illustrating exemplary hardware and/or software components of an exemplary computing device on which the processing device may be implemented according to some embodiments of the present disclosure.

FIG. 8 is a schematic diagram illustrating exemplary hardware and/or software components of an exemplary computing device 800 on which the processing device 120 may be implemented according to some embodiments of the present disclosure. As illustrated in FIG. 8, the computing device 800 may include a processor 810, a storage 820, an input/output (I/O) 830, and a communication port 840.

The processor 810 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 810 may process imaging data obtained from the medical device 110, the terminal(s) 140, the storage device 130, a detection device, and/or any other component of the medical system 100. In some embodiments, the processor 810 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 800. However, it should be noted that the computing device 800 in the present disclosure may also include multiple processors. Thus operations and/or method steps that are performed by one processor as described in the present disclosure may also be jointly or separately performed by the multiple processors. For example, if in the present disclosure the processor of the computing device 800 executes both process A and process B, it should be understood that process A and process B may also be performed by two or more different processors jointly or separately in the computing device 800 (e.g., a first processor executes process A and a second processor executes process B, or the first and second processors jointly execute processes A and B).

The storage 820 may store data/information obtained from the medical device 110, the terminal(s) 140, the storage device 130, a detection device, and/or any other component of the medical system 100. The storage 820 may be similar to the storage device 130 described in connection with FIG. 1, and the detailed descriptions are not repeated here.

The I/O 830 may input and/or output signals, data, information, etc. In some embodiments, the I/O 830 may enable a user interaction with the processing device 120. In some embodiments, the I/O 830 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 840 may be connected to a network (e.g., the network 150) to facilitate data communications. The communication port 840 may establish connections between the processing device 120 and the medical device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 840 may be and/or include a standardized communication port, such as RS232, RS485. In some embodiments, the communication port 840 may be a specially designed communication port. For example, the communication port 840 may be designed in accordance with the digital imaging and communications in medicine (DICOM) protocol.

Figure 9:
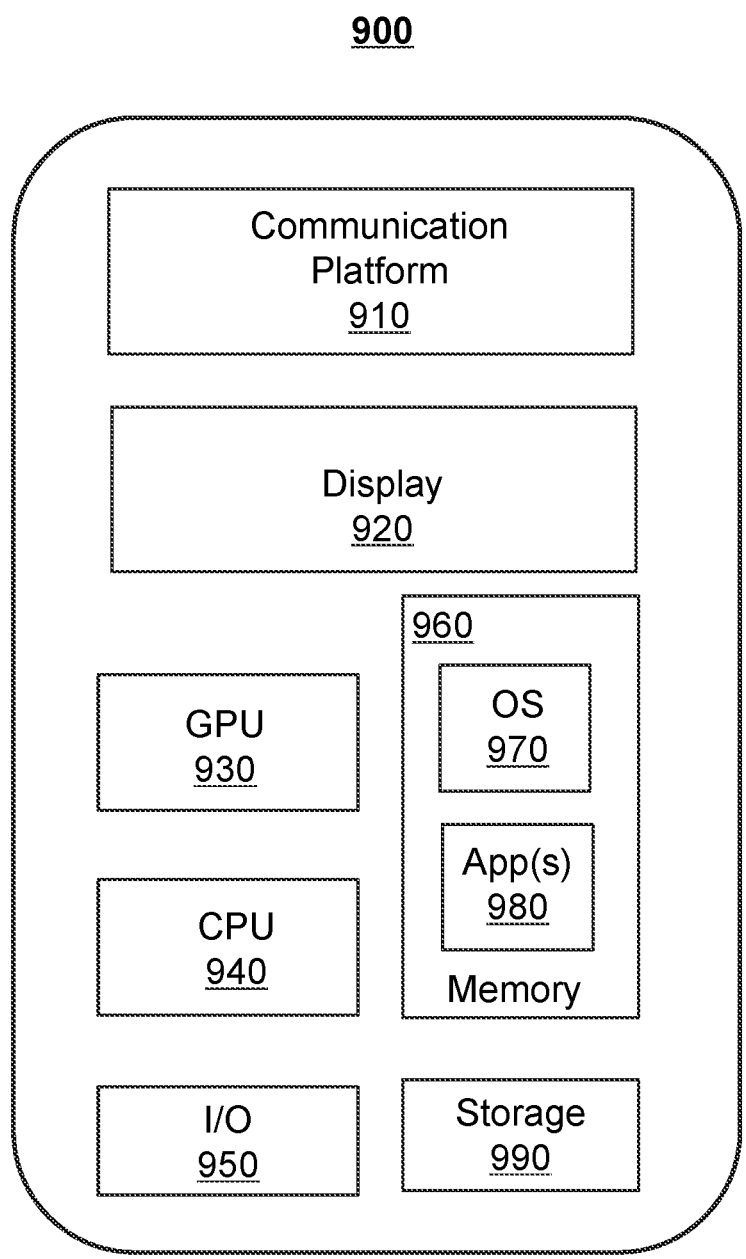
FIG. 9 is a schematic diagram illustrating exemplary hardware and/or software components of an exemplary mobile device on which the terminal(s) may be implemented according to some embodiments of the present disclosure.

FIG. 9 is a schematic diagram illustrating exemplary hardware and/or software components of an exemplary mobile device 900 on which the terminal(s) 140 may be implemented according to some embodiments of the present disclosure.

As illustrated in FIG. 9, the mobile device 900 may include a communication platform 910, a display 920, a graphics processing unit (GPU) 930, a central processing unit (CPU) 940, an I/O 950, a memory 960, and a storage 990. In some embodiments, any other suitable component, including but not limited to a system bus or a controller (not shown), may also be included in the mobile device 900.

In some embodiments, the communication platform 910 may be configured to establish a connection between the mobile device 900 and other components of the medical system 100, and enable data and/or signal to be transmitted between the mobile device 900 and other components of the medical system 100. For example, the communication platform 910 may establish a wireless connection between the mobile device 900 and the medical device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 910 may also enable the data and/or signal between the mobile device 900 and other components of the medical system 100. For example, the communication platform 910 may transmit data and/or signals inputted by a user to other components of the medical system 100. The inputted data and/or signals may include a user instruction. As another example, the communication platform 910 may receive data and/or signals transmitted from the processing device 120. The received data and/or signals may include imaging data acquired by a detector of the medical device 110.

In some embodiments, a mobile operating system (OS) 970 (e.g., iOS™ Android™, Windows Phone™, etc.) and one or more applications (App(s)) 980 may be loaded into the memory 960 from the storage 990 in order to be executed by the CPU 940. The applications 980 may include a browser or any other suitable mobile apps for receiving and rendering information respect to a field map determination operation or other information from the processing device 120. User interactions with the information stream may be achieved via the I/O 950 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 10:
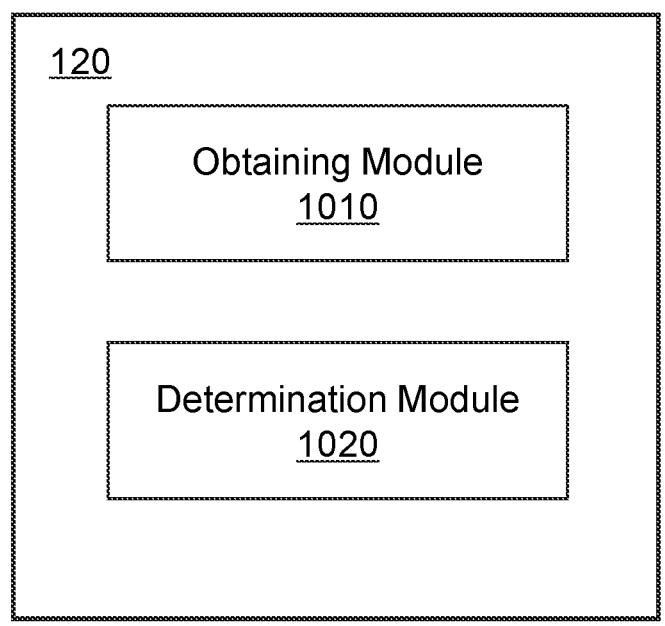
FIG. 10 is a schematic diagram illustrating an exemplary processing device according to some embodiments of the present disclosure.

FIG. 10 is a schematic diagram illustrating an exemplary processing device according to some embodiments of the present disclosure. In some embodiments, the processing device 120 may include an obtaining module 1010 and a determination module 1020.

The obtaining module 1010 may be configured to obtain data and/or information associated with the medical system 100. The data and/or information associated with the medical system 100 may include detection data of a subject, motion data of a subject, an image of a subject, or the like, or any combination thereof. For example, the obtaining module 1010 may obtain detection data of a subject located in a field of view (FOV) of a medical device. In some embodiments, the obtaining module 1010 may obtain the data and/or the information associated with the medical system 100 from one or more components (e.g., the medical device 110, the storage device 130, the terminal 140, at least one detection device) of the medical system 100 via the network 150.

The determination module 1020 may be configured to determine data and/or information associated with the image processing system 100. In some embodiments, the determination module 1020 may determine motion data of a subject based on detection data. For example, the determination module 1020 may extract posture data of the subject from the detection data. As another example, the determination module 1020 may extract physiological motion data of the subject from the detection data. In some embodiments, the determination module 1020 may generate, based on motion data, a control signal for controlling a medical device to scan a subject. In some embodiments, the determination module 1020 may generate an image of a subject based on a scan of the subject. The determination module 1020 may perform an artifact correction on the image of the subject based on the motion data. In some embodiments, the determination module 1020 may determine a region of interest (ROI) of the subject. The determination module 1020 may extract, from detection data of the subject, a detection data sub-set of the ROI of the subject. The determination module 1020 may determine the motion data of the subject based on the detection data sub-set of the ROI of the subject.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the obtaining module 1010 and the determination module 1020 may be combined into a single module. In some embodiments, one or more modules may be added or omitted in the processing device 120. For example, the processing device 120 may further include a storage module (not shown in FIG. 10) configured to store data and/or information (e.g., the detection data, the motion data) associated with the medical system 100.

Figure 11:
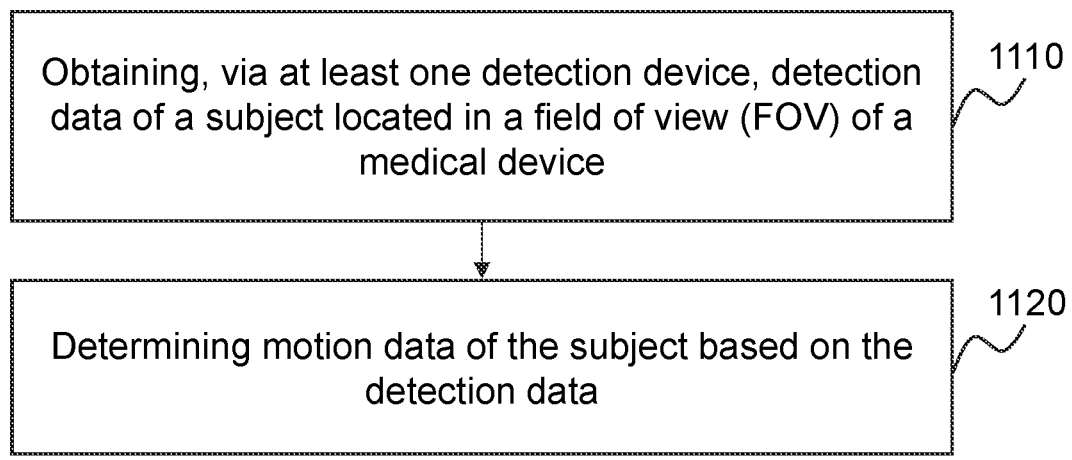
FIG. 11 is a flowchart illustrating an exemplary process for determining motion data of a subject according to some embodiments of the present disclosure.

FIG. 11 is a flowchart illustrating an exemplary process for determining motion data of a subject according to some embodiments of the present disclosure. In some embodiments, the process 1100 may be implemented in the medical system 100 illustrated in FIG. 1. For example, the process 1100 may be stored in the storage device 130 and/or the storage (e.g., the storage 820, the storage 990) as a form of instructions, and invoked and/or executed by the processing device 120 (e.g., the processor 810 of the computing device 800 as illustrated in FIG. 8, the CPU 940 of the mobile device 900 as illustrated in FIG. 9). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1110, the processing device 120 (e.g., the obtaining module 1010) may obtain, via at least one detection device (e.g., the detection device 30 illustrated in FIGS. 2 and 4-7), detection data of a subject located in a field of view (FOV) of a medical device (e.g., the medical device 110 illustrated in FIG. 1, the MRI device 20 illustrated in FIGS. 2 and 4-7).

In some embodiments, the subject may undergo a motion (e.g., a posture motion, a physiological motion) during and/or before a scan performed by the medical device. The at least one detection device may be configured to obtain detection data relating to the motion of the subject during and/or before the scan. The motion of the subject may include a posture motion and a physiological motion. As used herein, a posture motion of the subject refers to a rigid motion of a portion (e.g., the head, a leg, a hand) of the subject. For example, the rigid motion may include a translational and/or rotational motion of the portion of the subject. Exemplary rigid motion may include the rotating or nodding of the head of the subject, legs motion, hands motion, and so on. The physiological motion may include a cardiac motion, a respiratory motion, a blood flow, a gastrointestinal motion, a skeletal muscle motion, a brain motion (e.g., a brain pulsation), or the like, or any combination thereof.

In some embodiments, the detection device may be a non-contact detection device as described elsewhere in the present disclosure. In some embodiments, the detection device may include an FMCW radar. The emission frequency of the FMCW radar may be greater than 60 GHz. The radar may emit a reference signal (e.g., an RF sweep signal) to an FOV of the radar, and the reference signal may be reflected by the subject. The radar may receive at least a portion of the reflected reference signal (e.g., an RF echo signal) from the subject. The detection data may include the reference signal, the received reflected reference signal, image data (e.g., point-cloud data) generated based on the reference signal and the received reflected reference signal, or the like, or any combination thereof.

Information (e.g., a frequency difference, a phase difference) relating to the reflected reference signal and the reference signal may reflect the motion of the subject (e.g., a moving velocity, a moving direction, a displacement of the subject from a reference position), and be used to determine the motion data of the subject. For example, a distance between the radar and a body surface of the subject may be measured based on a frequency difference and/or a phase difference between an RF sweep signal and an RF echo signal. The variation of the distance between the radar and the body surface of the subject over a time period may be used to detect the motion of the subject.

In some embodiments, the at least one detection device may include a plurality of detection devices. The processing device 120 may obtain a detection data sub-set from each of the plurality of detection devices. The detection data sub-set may be acquired by monitoring, via the each detection device, at least part of the subject in an FOV of the each detection device. The processing device 120 may further obtain the detection data of the subject by merging, based on the FOV of the each detection device, the detection data sub-sets of the plurality of detection devices. Merely by way of example, the at least one detection device may include a first detection device (e.g., a first detection device 3001 illustrated in FIG. 7) and a second detection device (e.g., a second detection device 3002 illustrated in FIG. 7). A first FOV of the first detection device and a second FOV of the second detection device may not overlap, partially overlap, or completely overlap.

In some embodiments, if the first FOV of the first detection device and the second FOV of the second detection device do not overlap, a first detection data sub-set may be obtained from the first detection device, and a second detection data sub-set may be obtained from the second detection device. The detection data of the subject may be obtained by combining the first detection data sub-set and the second detection data sub-set.

In some embodiments, if the first FOV of the first detection device and the second FOV of the second detection device partially overlap, a detection data sub-set corresponding to an overlap region obtained from the first detection device or the second detection device may be determined as detection data corresponding to the overlap region. Alternatively, the detection data corresponding to the overlap region may be determined by performing a non-weighted or weighted merging operation on a first detection data sub-set corresponding to the overlap region obtained from the first detection device and a second detection data sub-set corresponding to the overlap region obtained from the second detection device. For example, the processing device 120 may determine a first weighted detection data sub-set by multiplying the first detection data sub-set corresponding to the overlap region by a first weight, and a second weighted detection data sub-set by multiplying the second detection data sub-set corresponding to the overlap region by a second weight. The processing device 120 may determine the detection data corresponding to the overlap region by summing the first weighted detection data sub-set and the second weighted detection data sub-set. For example, the processing device 120 may determine the detection data corresponding to the overlap region by summing frequency values or phase values of the first weighted detection data sub-set and the second weighted detection data sub-set. For the non-overlapping region of an FOV of a detection device, the detection data sub-set obtained by the detection device may be used. For instance, for the non-overlapping region of the first FOV of the first detection device, the detection data sub-set obtained by the first detection device may be used. As another example, for the non-overlapping region of the second FOV of the second detection device, the detection data sub-set obtained by the second detection device may be used.

In some embodiments, if the first FOV of the first detection device and the second FOV of the second detection device completely overlap, the detection data may be determined by performing a non-weighted or weighted merging operation on the first detection data sub-set obtained from the first detection device and the second detection data sub-set obtained from the second detection device. As another example, a detection data sub-set obtained from the first detection device (or the second detection device) may be used to verify a detection data sub-set obtained from the second detection device (or the first detection device).

In some embodiments, the processing device 120 may obtain the detection data from the at least one detection device. Alternatively, the detection data may be acquired by the at least one detection device and stored in a storage device (e.g., the storage device 130, or an external source). The processing device 120 may retrieve the detection data from the storage device. In some embodiments, the processing device 120 may obtain the detection data from the at least one detection device in real time or intermittently (e.g., periodically or irregularly).

In 1120, the processing device 120 (e.g., the determination module 1020) may determine motion data of the subject based on the detection data.

The motion data may reflect a motion state of the subject. In some embodiments, the motion data may include posture data of the subject and physiological motion data of the subject. The posture data may reflect the posture motion of the subject. The physiological motion data may reflect the motion of tissue or an organ that is caused or influenced by the physiological motion of the subject. In some embodiments, the motion data may include information relating to a corresponding motion of the subject. The information relating to a physiological motion may include a motion rate, a motion amplitude (or displacement), a motion cycle, a motion phase, or the like, or any combination thereof. In some embodiments, the motion data may include an electrocardiogram (ECG) signal relating to the cardiac motion of the subject, a respiratory signal relating to a respiratory motion of the subject, a posture signal relating to the posture motion of the subject, or the like. For example, the ECG signal may indicate cardiac cycle(s) of the subject, as well as changes of the heart rate and/or cardiac motion amplitude over the cardiac cycle(s). A cardiac cycle may include a plurality of cardiac phases, such as systole (during which the left and right ventricles contract and eject blood into the aorta and pulmonary artery, respectively) and diastole (during which the ventricles are relaxed). As another example, the respiratory signal may indicate a respiratory cycle of the subject, as well as a respiratory displacement, a respiratory rate, and/or a respiratory frequency, or the like. The respiratory cycle may include a plurality of respiratory phases, such as an inspiratory phase (during which the chest of the subject expands and air flows into the lungs) and an expiratory phase (during which the chest shrinks and air is pushed out of the lungs).

In some embodiments, the processing device 120 may extract the posture data of the subject from the detection data. For example, the processing device 120 may determine contour data of the subject based on the detection data. A contour of the subject may be formed by an edge of the surface of the subject. The contour data may reflect the motion of the contour of the subject. For example, the contour data may include a moving velocity (or a variation range of the moving velocity in a time period) of at least one position of a plurality of positions of the contour of the subject, a moving direction of at least one position of the plurality of positions of the contour of the subject, a displacement of at least one position of the plurality of positions of the contour of the subject from a reference position, point cloud data of the contour of the subject, or the like, or any combination thereof. As used herein, point cloud data of a subject refers to a set of data points associated with the subject.

The processing device 120 may determine the posture data based on the contour data. In some embodiments, the processing device 120 may obtain a plurality of point cloud frames corresponding to a plurality of time points or a plurality of time periods acquired by the at least one detection device. The processing device 120 may then determine the posture data based on the plurality of point cloud frames. For example, the processing device 120 may determine the posture data by tracking a motion of at least one body landmark of the subject over the plurality of time points or the plurality of time periods. The at least one body landmark may include one or more representative body regions or features of the subject, such as one or more anatomical joints, a shoulder, an ankle, the waist, a knee, a groin, or the like, or any combination thereof.

Figure 12A:
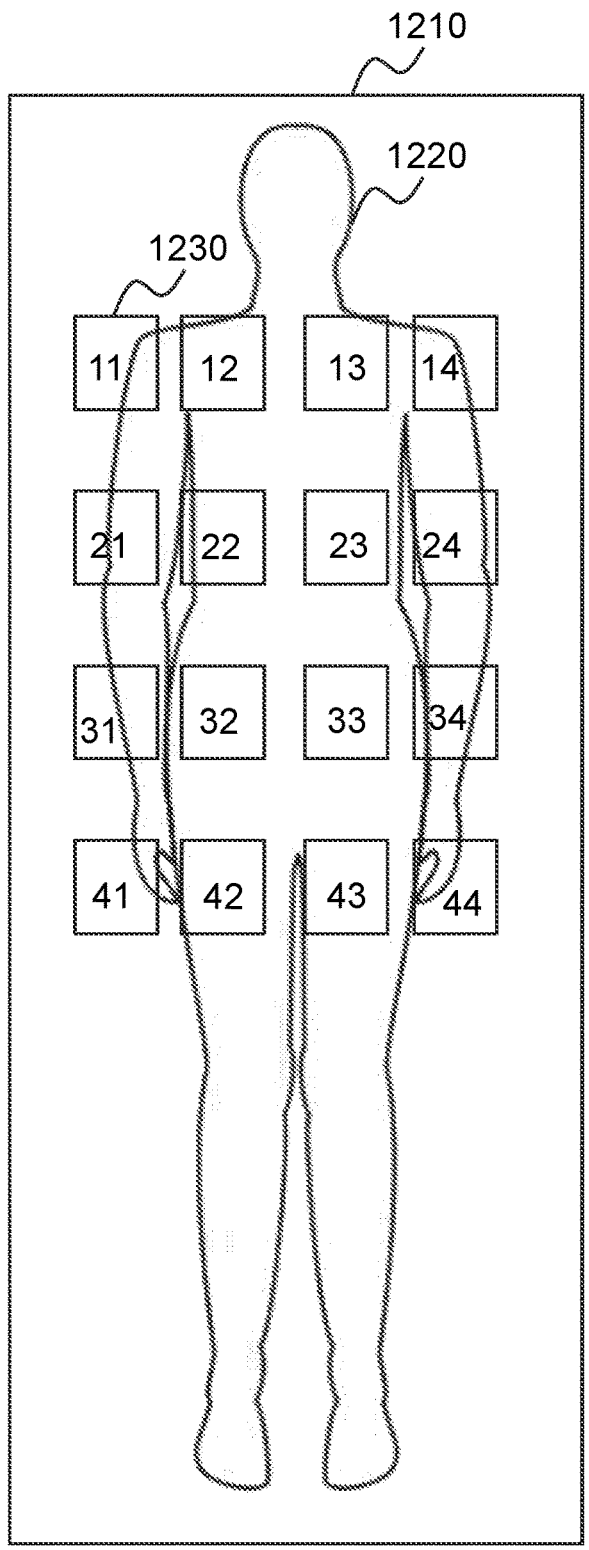
FIGS. 12A and 12B are schematic diagrams illustrating a posture motion of a subject according to some embodiments of the present disclosure.
Figure 12B:
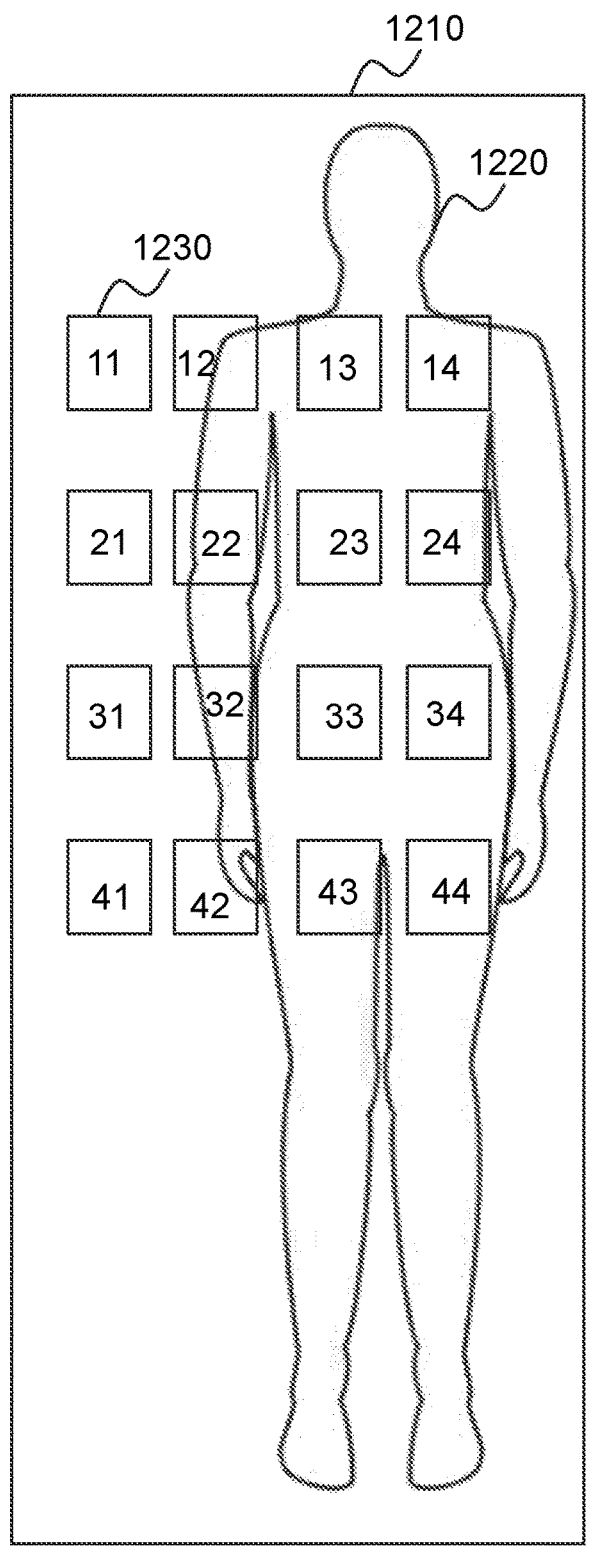

In some embodiments, the processing device 120 may determine the posture data based on moving velocities of at least one position of a plurality of positions of the contour of the subject corresponding to a plurality of time points or a plurality of time periods. Merely by way of example, as illustrated in FIGS. 12A and 12B, a process for determining the posture data based on contour data (e.g., instantaneous velocities of sixteen detection positions) obtained by a 4×4 radar array is taken as an example. As illustrated in FIG. 12A, a subject 1220 may be placed on a scanning table 1210 at a time point T1. The 4×4 radar array may include sixteen radar units 1230. Each radar unit 1230 may correspond to a detection position (e.g., a detection position 11, a detection position 12, . . . , a detection position 44). During a scan of the subject by a medical device, a position of the 4×4 radar array relative to the scanning table 1210 may be fixed. If the moving velocities (e.g., the instantaneous velocities) of the sixteen detection positions obtained by the 4×4 radar array at the time point T1 as illustrated in FIG. 12A are represented according to Equation (1):

$$V = \begin{bmatrix} v_{11} & v_{12} & v_{13} & v_{14} \\ v_{21} & v_{22} & v_{23} & v_{24} \\ v_{31} & v_{32} & v_{33} & v_{34} \\ v_{41} & v_{42} & v_{43} & v_{44} \end{bmatrix}, \quad (1)$$

where V refers to a moving velocity matrix at the time point T1; $v_{11}$ refers to a moving velocity of the detection position 11 at the time point T1; $v_{12}$ refers to a moving velocity of the detection position 12 at the time point T1; $v_{13}$ refers to a moving velocity of the detection position 13 at the time point T1, and so on. The moving velocities (e.g., instantaneous velocities) of the sixteen detection positions obtained by the 4×4 radar array at a time point T2 after T1 as illustrated in FIG. 12B are represented according to Equation (2):

$$V' = \begin{bmatrix} 0 & v'_{12} & v'_{13} & v'_{14} \\ 0 & v'_{22} & v'_{23} & v'_{24} \\ 0 & v'_{32} & v'_{33} & v'_{34} \\ 0 & v'_{42} & v'_{43} & v'_{44} \end{bmatrix}, \quad (2)$$

where V' refers to a moving velocity matrix at the time point T2; $v_{12}'$ refers to a moving velocity of the detection position 12 at the time point T2; $v_{13}'$ refers to a moving velocity of the detection position 13 at the time point T2, and so on. The moving velocities of the detection position 11, the detection position 21, the detection position 31, and the detection position 41 is 0. It may indicate that the subject 1220 moves to the right of the scanning table 1210 such that the subject 1220 is outside the detection positions 11, 21, 31, and 41, as illustrated in FIG. 12B.

Further, the processing device 120 may extract the physiological motion data of the subject from the detection data. In some embodiment, the processing device 120 may extract the cardiac motion data and the respiratory motion data from the detection data based on a frequency range of the respiratory motion and a frequency range of the cardiac motion according to a spectrum analysis. The frequency range of the cardiac motion and the frequency range of the cardiac motion may be manually set by a user of the medical system 100, or be determined by one or more components (e.g., the processing device 120) of the medical system 100 according to different situations. For a normal person, the frequency range of the cardiac motion may be higher than the frequency range of the cardiac motion. For example, the processing device 120 may generate filtered detection data by performing a filtering operation on the detection data to filter out a disturbed signal (e.g., the posture data). The processing device 120 may transform the filtered detection data from the time domain to the frequency domain by performing a Fourier transformation on the filtered detection data. The processing device 120 may then extract the cardiac motion data and the respiratory motion data from the filtered detection data in the frequency domain based on the frequency range of the respiratory motion and the frequency range of the cardiac motion. The processing device 120 may further determine the cardiac motion data and the respiratory motion data in the time domain by performing an inverse Fourier transform on the cardiac motion data and the respiratory motion data in the frequency domain, respectively.

In some embodiments, the medical system 100 may include a plurality of detection devices, the processing device 120 may obtain a detection data sub-set from each of the plurality of detection devices. The processing device 120 may determine the motion data by performing an averaging operation on a plurality of detection data sub-sets obtained from the plurality of detection devices. For example, the processing device 120 may determine an average value of the plurality of detection data sub-sets obtained from the plurality of detection devices. The processing device 120 may determine the respiratory motion data based on a variation of the average value over a time period. The processing device 120 may then determine a target detection data sub-set of each detection device of the plurality of detection devices by subtracting the average value from the detection data sub-set of the each detection device. The processing device 120 may further determine the cardiac motion data based on the target detection data sub-set of each detection device of the plurality of detection devices.

According to some embodiments of the present disclosure, the motion data may be determined based on the plurality of detection data sub-sets obtained from the plurality of detection devices, which may avoid or reduce the influence of the position of the detection device on the obtaining of the detection data, and improve the accuracy of the motion data. In addition, the motion data may be determined by performing an averaging operation on the plurality of detection data sub-sets obtained from the plurality of detection devices, which may reduce or eliminate the influence of posture motion data on the determination of the physiological motion data.

In some embodiments, the processing device 120 may generate, based on the motion data, a control signal for controlling the medical device to scan the subject. In some embodiments, the control signal may involve the gating technique. The control signal may be used to control the medical device. Taking an MRI device as an example, the control signal may be used to cause the MRI device to start, terminate, or pause an MRI scan. In some embodiments, the processing device 120 may determine a time point (or period) in which the physiological motion of the subject is smooth or minimal based on the motion data. MR signals acquired in such a period may be less affected by physiological motion and have higher signal quality compared with MR signals acquired in other periods (e.g., the systole). This may reduce physiological motion-induced artifacts in a resulting image. For example, the physiological motion at a certain time point may be regarded as being smooth or minimal if the motion amplitude at the certain time point is below a first threshold. As another example, the physiological motion in a certain period may be regarded as being smooth or minimal if, for example, a change of the motion amplitude of the physiological motion within the period is below a second threshold, or the like.

Further, the processing device 120 may determine an MR signal acquisition time based on the motion data. The MR signal acquisition time may be a time point (or period) when the MRI device is controlled to execute an MR scan on the subject. For example, the MR signal acquisition time may include a time point or period in which the physiological motion of the subject is smooth. The processing device 120 may transmit the control signal to the MRI device to execute the MR scan. By determining a suitable MR signal acquisition time based on the motion data, an image reconstructed based on MR signals detected in the MR scan may have less motion artifact and higher quality.

In some embodiments, the processing device 120 may generate an image (e.g., an MR image) of the subject based on the scan (e.g., an MR scan). The processing device 120 may perform an artifact correction on the image of the subject based on the motion data. For example, the motion data may include information regarding a respiratory signal. The processing device 120 may utilize a respiratory compensation technique, such as a respiratory ordered phase encoding (ROPE) technique, a centrally ordered phase encoding (COPE) technique, a hybrid ordered phase encoding (HOPE), or the like, or any combination thereof in the MR image reconstruction. For example, based on information regarding a respiratory signal, the processing device 120 may apply a same phase encoding or similar phase encodings to MR signals corresponding to a same respiratory phase or similar respiratory phases in the MR image reconstruction. In the resulting MR image, motion artifacts may be eliminated or partially eliminated.

According to some embodiments of the present disclosure, the motion data (e.g., the posture data and/or the physiological motion data) of the subject may be determined based on the detection data acquired by at least one FMCW radar with an emission frequency greater than 60 GHz. Conventionally, a radar with an emission frequency of 24 GHz may be used to detect the motion of the subject. For example, an RF sweep signal of a first frequency bandwidth may be used to detect the movement of a lung to obtain respiratory motion data, and an RF sweep signal of a second frequency bandwidth may be used to detect the movement of the heart to obtain the cardiac motion data. As another example, an RF sweep signal of a specific frequency bandwidth may be used to detect the movement of the heart and the lung at the same time, and then the cardiac motion data and the respiratory motion data may be obtained and separated according to a spectrum analysis algorithm.

Compared to a wavelength (e.g., 10 mm) of an RF sweep signal emitted by the radar with the emission frequency of 24 GHz, a wavelength (e.g., 5 mm) of an RF sweep signal emitted by the FMCW radar with the emission frequency of 60 GHz or higher as disclosed herein may be relatively small. The detection accuracy of the FMCW radar with the emission frequency of 60 GHz or higher may be higher than the radar with the emission frequency of 24 GHz, and it is suitable for detecting the movement of the thoracic cavity surface of the subject caused by one or more physiological motion (e.g., the cardiac motion and/or the respiratory motion) of the subject. Furthermore, compared to a radar with the emission frequency of 24 GHz, the size of a transmitting antenna and/or a receiving antenna of the FMCW radar may be relatively small, which may make it easy to be integrated in or mounted on the medical device (e.g., an MRI device).

In addition, compared with the RF sweep signal emitted by the radar with the emission frequency of 24 GHz, a difference between a frequency (e.g., 60 GHz or higher) of the RF sweep signal emitted by the FMCW radar disclosed herein and the working frequency of an MRI device may be relatively large. Accordingly, the FMCW radar may have a strong anti-interference ability when applied in the MRI device.

According to some embodiments of the present disclosure, when the subject breathes uniformly, each position on a body surface of the subject may exhibit a specific regular undulating motion, and feature information (e.g., a moving amplitude, a moving velocity, a moving direction) of the undulating motion of a specific position may be different from that of other positions on the body surface of the subject. Accordingly, the motion data of the subject may be determined based on the feature information of the undulating motion of one or more positions on the body surface of the subject acquired by the at least one detection device.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may determine a region of interest (ROI) of the subject. As used herein, an ROI refers to a region (e.g., an organ, tissue, a body portion) to be scanned and/or a region (e.g., an organ, tissue, a body portion) that may be significantly influenced by the physiological motion of a subject. For example, the ROI may include the chest, the abdomen, the neck, or the like, of the subject. The processing device 120 may then extract, from the detection data of the subject, a detection data sub-set of the ROI of the subject. Further, the processing device 120 may determine the motion data of the subject based on the detection data sub-set of the ROI of the subject. According to some embodiments of the present disclosure, by extracting the detection data sub-set of the ROI from the detection data of the subject, the amount of data required for motion data determination may be reduced. In addition, the interference of regions other than the ROI in the motion data determination may be reduced or eliminated.

In some embodiments, in response to determining that the posture data of the subject is detected during an operation, e.g., a scan of the subject, the processing device 120 may cause the medical device to terminate or pause the operation. Thus, the quality of the operation, e.g., assessed based on the quality of an image generated based on the scan, may be improved and the operation time may be saved.

In some embodiments, the medical system 100 may include a plurality of detection devices, and the processing device 120 may select at least one detection device from the plurality of detection devices based on a location of the subject and a location of the each detection device. The selected at least one detection device may be directed to obtain the detection data of the subject. For example, the processing device 120 may select the at least one detection device located close to the heart of the subject to detect the detection data relating to the cardiac motion of the subject.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A method for motion detection implemented on a computing device having at least one processor and at least one storage device, the method comprising:

obtaining detection data of a subject located in a field of view (FOV) of a medical device, the detection data being collected by a plurality of frequency modulated continuous wave (FMCW) radar mounted outside the FOV of the medical device, and the plurality of FMCW radars collecting the detection data by radiating continuous waves toward the subject; and simultaneously determining posture data relating to a posture motion of the subject and physiological motion data relating to a physiological motion of the subject based on the detection data; and generating, based on the posture data and the physiological motion data, a control signal for controlling the medical device to scan the subject, wherein the posture data and the physiological motion data are determined by:

determining instantaneous velocities of a plurality of detection positions on the subject at least two time points based on the detection data;

determining the posture data according to the instantaneous velocities of the plurality of detection positions;

generating filtered detection data by filtering the posture data out from the detection data;

transforming the filtered detection data from the time domain to the frequency domain;

extracting, from the filtered detection data in the frequency domain, cardiac motion data and respiratory motion data in the frequency domain based on a frequency range of the respiratory motion and a frequency range of the cardiac motion; and determining cardiac motion data and respiratory motion data in the time domain by transforming the cardiac motion data and respiratory motion data in the frequency domain, wherein:

the plurality of FMCW radars have fixed positions and have FOVs that partially overlap, a total FOV of the plurality of FMCW radars covers the FOV of the medical device, and the obtaining detection data of the subject located in the FOV of the medical device comprises:

for each of the plurality of FMCW radars, obtaining a detection data sub-set acquired by the FMCW radar by monitoring at least part of the subject in the FOV of the FMCW radar;

determining an overlapping region and a non-overlapping region of the FOVs of the plurality of FMCW radars based on the FOVs of the plurality of FMCW radars; and obtaining the detection data of the subject by merging the detection data sub-sets of the plurality of FMCW radars based on the overlapping region and the non-overlapping region.

2. The method of claim 1, wherein the control signal involves a gating technique.

3. The method of claim 1, further comprising:
causing the medical device to perform, according to the control signal, a scan on the subject;
generating an image of the subject based on the scan, wherein a motion compensation technique is applied based on the posture data and the physiological motion data during the reconstruction of the image.

4. The method of claim 1, further comprising:
determining a region of interest (ROI) of the subject;
extracting, from the detection data of the subject, a detection data sub-set of the ROI of the subject; and
determining the posture data and the physiological motion data of the subject based on the detection data sub-set of the ROI of the subject.

5. The method of claim 1, wherein an emission frequency of the FMCW radar is greater than 60 GHz.

6. The method of claim 1, wherein the medical device is a magnetic resonance imaging (MRI) device.

7. A system for motion detection, comprising:
at least one storage device storing a set of instructions; and
at least one processor in communication with the at least one storage device, when executing the stored set of instructions, the at least one processor causes the system to perform operations including:
obtaining detection data of a subject located in a field of view (FOV) of a medical device, the detection data being collected by a plurality of frequency modulated continuous wave (FMCW) radars mounted outside the FOV of the medical device, and the plurality of FMCW radars collecting the detection data by radiating continuous waves toward the subject; and
simultaneously determining posture data relating to a posture motion of the subject and physiological motion data relating to a physiological motion of the subject based on the detection data; and
generating, based on the posture data and the physiological motion data, a control signal for controlling the medical device to scan the subject, wherein the posture data and the physiological motion data are determined by:
determining instantaneous velocities of a plurality of detection positions on the subject at least two time points based on the detection data;
determining the posture data according to the instantaneous velocities of the plurality of detection positions;
generating filtered detection data by filtering the posture data out from the detection data;
performing a filtering operation on the detection data to determine filtered detection data, a portion filtered out from the detection data including the posture data;
transforming the filtered detection data from the time domain to the frequency domain;

extracting, from the filtered detection data in the frequency domain, cardiac motion data and respiratory motion data in the frequency domain based on a frequency range of the respiratory motion and a frequency range of the cardiac motion; and determining cardiac motion data and respiratory motion data in the time domain by transforming the cardiac motion data and respiratory motion data in the frequency domain, wherein:

the plurality of FMCW radars have fixed positions and have FOVs that partially overlap, and a total FOV of the plurality of FMCW radars covers the FOV of the medical device, and the obtaining detection data of the subject located in the FOV of the medical device comprises:

for each of the plurality of FMCW radars, obtaining a detection data sub-set acquired by the FMCW radar by monitoring at least part of the subject in the FOV of the FMCW radar;

determining an overlapping region and a non-overlapping region of the FOVs of the plurality of FMCW radars based on the FOVs of the plurality of FMCW radars; and obtaining the detection data of the subject by merging the detection data sub-sets of the plurality of FMCW radars based on the overlapping region and the non-overlapping region.

8. The system of claim 7, wherein the control signal involves a gating technique.

9. The system of claim 7, the operations further comprising:
causing the medical device to perform, according to the control signal, a scan on the subject;
generating an image of the subject based on the scan, wherein a motion compensation technique is applied based on the posture data and the physiological motion data during the reconstruction of the image.

10. The method of claim 7, the operations further comprising:
determining a region of interest (ROI) of the subject;
extracting, from the detection data of the subject, a detection data sub-set of the ROI of the subject; and
determining the posture data and the physiological motion data of the subject based on the detection data sub-set of the ROI of the subject.

11. The system of claim 7, wherein an emission frequency of the FMCW radar is greater than 60 GHz.

12. The system of claim 7, wherein the medical device is a magnetic resonance imaging (MRI) device.

13. A non-transitory computer readable medium, comprising at least one set of instructions, wherein when executed by at least one processor of a computing device, the at least one set of instructions cause the at least one processor to effectuate a method comprising:
obtaining detection data of a subject located in a field of view (FOV) of a medical device, the detection data being collected by a plurality of frequency modulated continuous wave (FMCW) radars mounted outside the FOV of the medical device, and the plurality of FMCW radars collecting the detection data by radiating continuous waves toward the subject; and
simultaneously determining posture data relating to a posture motion of the subject and physiological motion data relating to a physiological motion of the subject based on the detection data; and
generating, based on the posture data and the physiological motion data, a control signal for controlling the medical device to scan the subject, wherein the posture data and the physiological motion data are determined by:

determining instantaneous velocities of a plurality of detection positions on the subject at least two time points based on the detection data;

determining the posture data according to the instantaneous velocities of the plurality of detection positions;

generating filtered detection data by filtering the posture data out from the detection data;

performing a filtering operation on the detection data to determine filtered detection data, a portion filtered out from the detection data including the posture data;

transforming the filtered detection data from the time domain to the frequency domain;

extracting, from the filtered detection data in the frequency domain, cardiac motion data and respiratory motion data in the frequency domain based on a frequency range of the respiratory motion and a frequency range of the cardiac motion; and determining cardiac motion data and respiratory motion data in the time domain by transforming the cardiac motion data and respiratory motion data in the frequency domain, wherein:

the plurality of FMCW radars have fixed positions and have FOVs that partially overlap, and a total FOV of the plurality of FMCW radars covers the FOV of the medical device, and the obtaining detection data of the subject located in the FOV of the medical device comprises:

for each of the plurality of FMCW radars, obtaining a detection data sub-set acquired by the FMCW radar by monitoring at least part of the subject in the FOV of the FMCW radar;

determining an overlapping region and a non-overlapping region of the FOVs of the plurality of FMCW radars based on the FOVs of the plurality of FMCW radars; and obtaining the detection data of the subject by merging the detection data sub-sets of the plurality of FMCW radars based on the overlapping region and the non-overlapping region.

14. The non-transitory computer readable medium of claim 13, wherein the control signal involves a gating technique.

15. The non-transitory computer readable medium of claim 13, the method further comprising:

causing the medical device to perform, according to the control signal, a scan on the subject;

generating an image of the subject based on the scan, wherein a motion compensation technique is applied based on the posture data and the physiological motion data during the reconstruction of the image.

16. The non-transitory computer readable medium of claim 13, the method further comprising:

determining a region of interest (ROI) of the subject;

extracting, from the detection data of the subject, a detection data sub-set of the ROI of the subject; and determining the posture data and the physiological motion data of the subject based on the detection data sub-set of the ROI of the subject.

17. The non-transitory computer readable medium of claim 13, wherein an emission frequency of the FMCW radar is greater than 60 GHz.

18. The non-transitory computer readable medium of claim 13, wherein the medical device is a magnetic resonance imaging (MRI) device.

\* \* \* \* \*